United States Patent [19]

Vidal et al.

[11] Patent Number: 5,256,147
[45] Date of Patent: Oct. 26, 1993

[54] REUSABLE TROCAR WITH EASILY REPLACEABLE OBTURATOR

[75] Inventors: Claude Vidal; Russell J. Redmond, both of Santa Barbara, Calif.

[73] Assignee: Minnesota Mining and Manufacturing Company, St. Paul, Minn.

[21] Appl. No.: 899,751

[22] Filed: Jun. 17, 1992

[51] Int. Cl.⁵ .............................. A61B 17/34
[52] U.S. Cl. .................... 604/158; 604/274
[58] Field of Search ............... 604/164, 165, 158, 274

[56] References Cited

U.S. PATENT DOCUMENTS

| | | |
|---|---|---|
| 1,527,291 | 2/1925 | Zorraquin . |
| 2,001,638 | 5/1935 | Tornsjo . |
| 2,623,521 | 12/1952 | Shaw . |
| 2,630,803 | 3/1953 | Baran . |
| 2,882,598 | 4/1959 | Fidelman . |
| 3,713,447 | 1/1973 | Adair . |
| 3,774,604 | 11/1973 | Danielsson . |
| 3,789,852 | 2/1974 | Kim et al. . |
| 4,139,011 | 2/1979 | Benolt et al. . |
| 4,168,699 | 9/1979 | Hauser . |
| 4,177,814 | 12/1979 | Knepshield et al. . |
| 4,190,048 | 2/1980 | Sampson . |
| 4,403,617 | 9/1983 | Tretinyak . |
| 4,414,974 | 11/1983 | Dotson et al. . |
| 4,431,426 | 2/1984 | Groshong et al. . |
| 4,473,076 | 9/1984 | Williams et al. . |
| 4,535,773 | 8/1985 | Yoon . |
| 4,601,710 | 7/1986 | Moll . |
| 4,617,929 | 10/1986 | Gill . |
| 4,654,030 | 3/1987 | Moll et al. . |
| 4,747,831 | 5/1988 | Kulli . |
| 4,808,168 | 2/1989 | Warring . |
| 4,813,426 | 3/1989 | Haber et al. . |
| 4,902,280 | 2/1990 | Lander . |
| 4,903,390 | 2/1990 | Vidal et al. .................. 29/239 |
| 4,906,236 | 3/1990 | Alberts et al. . |
| 4,922,602 | 5/1990 | Mehl . |
| 4,931,042 | 6/1990 | Holmes et al. . |
| 4,952,207 | 8/1990 | Lemieux . |
| 4,955,870 | 9/1990 | Ridderheim et al. . |
| 4,976,684 | 12/1990 | Broadmax, Jr. . |
| 5,002,557 | 3/1991 | Hasson . |
| 5,030,206 | 7/1991 | Lander . |
| 5,057,082 | 10/1991 | Burchette, Jr. . |
| 5,066,288 | 11/1991 | Deniega et al. . |
| 5,104,382 | 4/1992 | Brinkerhoff et al. . |
| 5,114,407 | 5/1992 | Burbank . |
| 5,116,353 | 5/1992 | Green . |
| 5,119,983 | 6/1992 | Green et al. ................ 227/179 |
| 5,122,122 | 6/1992 | Allgood . |
| 5,152,754 | 10/1992 | Plyley et al. ................ 604/164 |
| 5,158,552 | 10/1992 | Borgia et al. ............... 604/165 |

FOREIGN PATENT DOCUMENTS

| | | |
|---|---|---|
| 0135364 | 3/1985 | European Pat. Off. . |
| 0265193 | 4/1988 | European Pat. Off. . |
| 0293123 | 11/1988 | European Pat. Off. . |
| 0479130A1 | 4/1992 | European Pat. Off. . |
| 1356386 | 6/1974 | United Kingdom . |

OTHER PUBLICATIONS

"The Source of Laparoscopic Innovation", by Origin Medsystems, Inc., Four (4) pages, dated 1992.
"Our Answer to the Disposables", by AeSclepios Surgical Endoscopy Inc., One (1) page.
"Laparoscopic Cholecystectomy", by Solos Endoscopy, Inc., Four (4) pages.
"Fine Instruments for Endoscopic Surgery", by Snowden-Pencer, Five (5) pages.

Primary Examiner—Paul J. Hirsch
Attorney, Agent, or Firm—Gary L. Griswold; Walter N. Kirn; Jeffrey J. Hohenshell

[57] ABSTRACT

A trocar for placement in the lumen of a cannula to facilitate inserting the cannula through a wall defining a body cavity is disclosed. The trocar has a replaceable tip portion which affords continuous sharp cutting surfaces even in a completely reusable trocar.

18 Claims, 6 Drawing Sheets

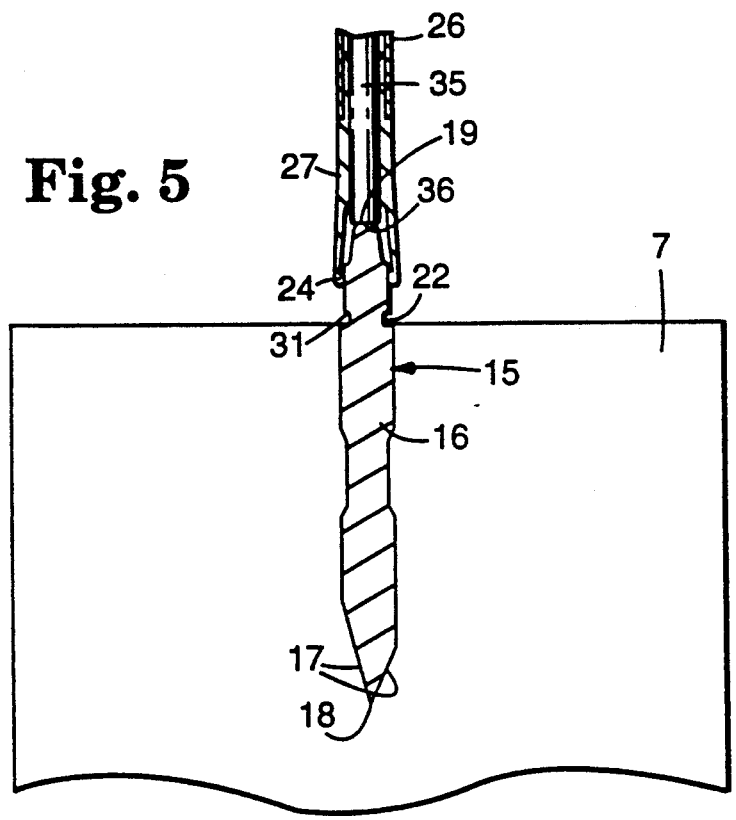
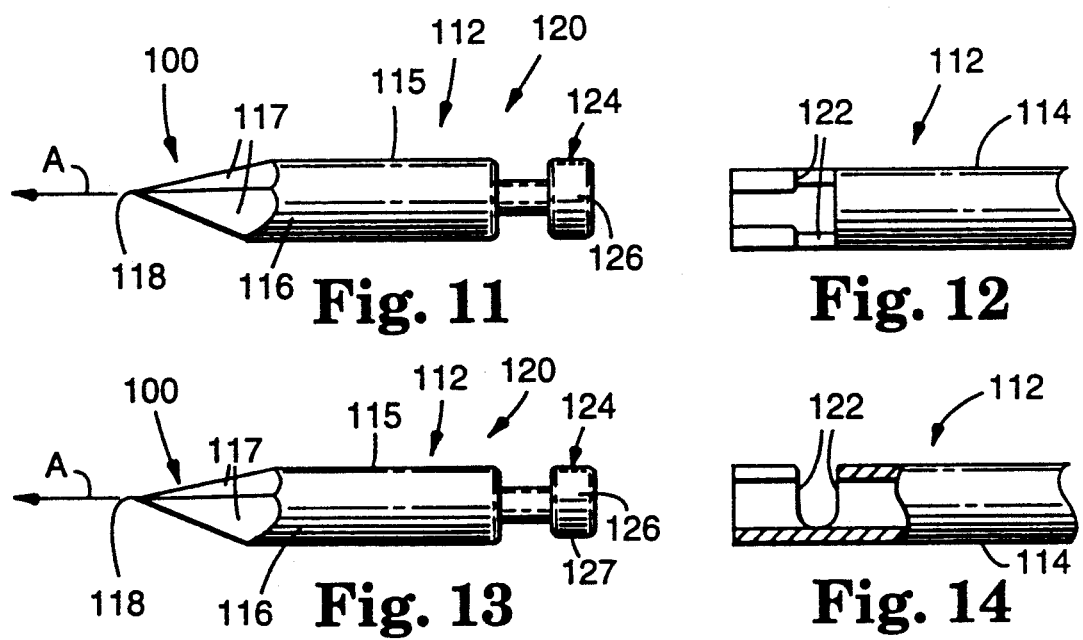

REUSABLE TROCAR WITH EASILY REPLACEABLE OBTURATOR

TECHNICAL FIELD

The present invention is directed to trocars for inserting an access tube or "cannula" through an abdominal wall, and more particularly to a reusable trocar having an easily replaceable obturator portion.

BACKGROUND OF THE INVENTION

An increasing number of abdominal surgical procedures are being performed with laparoscopic techniques in order to avoid a large skin incision. Typically in laparoscopic surgery, a special needle, similar to the pneumoneedles described in U.S. Pat. No. 4,808,168 to Warring and U.S. patent application No, 07/808,152 (both of which are herein expressly incorporated by reference), is inserted through the skin, and used to inflate the abdominal cavity with an insufflating gas such as $CO_2$. Once the abdomen is adequately dilated, the needle is removed and a rigid access tube or cannula with a larger diameter (for example 10 or 11 mm) is passed through the skin in the same location.

The access tube provides access for laparoscopes or other laparoscopic surgical tools such as the stapler described in U.S. Pat. No. 5,040,715 or the surgical clip appliers described in U.S. Pat. Nos. 5,084,057 and 5,100,420. To drive the access tube through the skin, the surgeon places a trocar obturator in the lumen of the access tube to provide a sharp, leading edge for cutting tissue.

The art is replete with trocar devices such as those shown in U.S. Pat. Nos. 4,535,773, 4,601,710, 4,654,030, 4,902,280, and 4,931,042. A prior art trocar device typically comprises a sharp point for penetrating the skin, surrounded by a spring-loaded protective sleeve. As these trocar devices are urged through the skin, friction with the skin causes the protective sleeve to slide proximally (rearwardly). After the access tube has penetrated through the skin, there is no longer friction between the protective sleeve and the skin, and the spring is designed to urge the protective sleeve distally (forwardly) to cover the sharp point, locking the protective sleeve in position to reduce the risk of accidental puncture of the underlying organs.

Two typical "safety" trocars currently available are known as the "Auto Suture Surgiport" T.M. (generally available from U.S. Surgical of Norwalk, Conn.) and the "Endopath" T.M. (generally available from Ethicon of Somerville, N.J.). Trocars similar, but not identical to these are shown in U.S. Pat. No. 5,066,288 and 5,030,206. These types of prior art trocar devices are generally used during a surgical procedure and then disposed of after the surgical procedure is completed. Such prior art trocars tend to be expensive, particularly when a "safety" mechanism is included. Also, the presence of a "shield" necessarily reduces the size of the obturator/knife used with a given size of cannula and may cause other problems for the user or patient.

A more cost effective alternative to a disposable trocar is a completely reusable trocar, such as the Trocars generally available from Snowden-Pencer, Inc. of Tucker, Ga. or the Trocars generally available from Solos, Endoscopy, Inc. of Duluth Ga. A reusable trocar typically comprises an obturator assembly having sharp surfaces for cutting tissue, and a cannula or access tube assembly.

The obturator assembly of a typical reusable trocar may be used on a patient and then cleaned and sterilized for reuse on the same or a different patient. Reusable trocars tend to have minimal parts to afford quick and convenient cleaning and sterilization of the trocars.

Reusable trocars tend to encounter problems as the sharp tissue cutting surfaces of the obturator (including the tip) of a completely reusable trocar tend to become dull after even a few uses. Such "dulling" of the cutting surfaces of the trocar generally tends to increase the insertion force required to insert the trocar into the abdominal cavity.

Additionally, the sharp tissue cutting surfaces of a reusable trocar are vulnerable to mechanical damage from mishandling or other abuse during cleaning, sterilization and handling. For example, if the cutting surfaces or tip of a reusable trocar impulsively impact a solid object (such as when the obturator is inadvertently dropped on the floor or working area), the tip of the obturator tends to take a highly undesirable "hook" shape.

U.S. Pat. No. 4,601,710 discloses a trocar assembly having a trocar tip attached to the rest of the trocar assembly by set screws or threads. Also, AeSclepios Surgical Endoscopy, Inc. of Montreal, Quebec Canada and General Medical of Richmond Va. are believed to currently sell a reusable trocar having a trocar tip that is attached to the rest of the trocar assembly by threads.

Threading the trocar tip to the rest of the trocar assembly is believed to be undesirable because it may be difficult for the user to determine when the trocar tip is completely screwed into the rest of the trocar assembly. Although some surgeons prefer that the trocar tip slightly rotate relative to the cannula during insertion, some surgeons prefer that the trocar tip remain stationary relative to the cannula during insertion. If the trocar is used when the trocar tip is not completely screwed into the rest of the trocar assembly, the trocar tip may rotate relative to the rest of the trocar assembly and the cannula. Again, some surgeons wish to avoid such action. Also, the threaded portion of such a trocar is believed to be difficult to clean or sterilize as in some procedures, it may expose a healthcare worker to relatively sharp threaded surfaces that may be contaminated.

Additionally, using a set screw to attach the trocar tip to the rest of the trocar assembly is believed to be cumbersome or difficult for the user, as a user is required to manipulate a potentially fine set screw.

BRIEF DESCRIPTION OF THE INVENTION

According to the present invention there is provided a reusable trocar assembly having an improved obturator which (1) affords sharp cutting surfaces even after repeated trocar uses, (2) has an obturator having a proximal portion and a distal end portion with sharp surfaces for cutting tissue, (3) affords firm retention of the distal end portion by the proximal portion while the obturator is inserted and removed from the patient's body, but which also affords easy convenient release of the distal end portion from the proximal portion to afford replacement of the used or dull distal end portion, (4) affords convenient and efficient disposal and replacement of a used or dull obturator distal end portion, (5) optionally includes a mechanism for releasing the distal end portion without requiring a user to grasp the distal end portion, (6) is inexpensive and easy to manufacture, (7) affords convenient, rapid sterilization and cleaning of its reusable portions, and (8) which is convenient and simple to use.

The present invention comprises a trocar assembly for placement in a cannula to facilitate inserting the cannula through a wall having tissue defining a body cavity. The cannula comprises interior surfaces defining a lumen and a distal end having an opening. The trocar assembly comprises a handle, and an obturator having an imaginary axis.

The obturator comprises a proximal portion, and a distal end portion comprising a base part and having cutting surfaces adapted to pierce the wall defining the body cavity.

The trocar assembly also comprises detent means for releasably connecting the proximal portion of the obturator to the distal end portion of the obturator. The detent means comprises a groove part extending at least partially about the axis of the obturator located on one of the proximal and distal end portions and a detent part situated on the other of the proximal and distal end portions and adapted to engage the groove part.

When the obturator is placed within the cannula, at least a portion of the groove part and the detent part are situated within the lumen of the cannula and the cutting surfaces project beyond the distal end of the cannula. In this configuration the detent part is "locked" to the groove part to restrict the chances of the distal end portion of the obturator falling into the patient.

Several species of trocar assemblies are shown and described. The trocar assemblies have various features. For example, a first embodiment of trocar assembly comprises means for restricting relative rotation between the distal end portion and the proximal portion comprising leaf spring members and ribs which mesh.

Both the first and a second embodiments of trocar assembly describe different means for releasing the distal end portion without requiring the user to grasp the distal end portion. The first embodiment describes an ejector rod having a distal end adapted to abut a proximal end of the distal end portion, and a button member mounted to the ejector rod and movable between a release and a rest position.

The second embodiment of trocar assembly describes a disposal container having first and second sections each having manually engagable outer surfaces and trocar distal end portion engaging surfaces. The disposal container's first and second portions are movable between an open position adapted to receive a distal end portion of a trocar assembly and a closed position. In the closed position (1) the distal end portion engaging surfaces grasp portions of the distal end portion of the obturator, (2) the disposal container encloses the cutting surfaces of the distal end portion and provides a barrier to restrict the user's exposure to the cutting surfaces, and (3) a user may grasp the manually engagable surfaces of the disposal container and move the disposal container axially away from the proximal portion of the trocar assembly to separate the distal end portion from the proximal portion.

In a third embodiment of the present invention, the detent means comprises a lug.

BRIEF DESCRIPTION OF THE DRAWINGS

The present invention will be further described with reference to the accompanying drawing wherein like reference numerals refer to like parts in the several views, and wherein:

FIG. 5 is a sectional view of the trocar assembly of FIG. 1 removed from the cannula assembly and illustrating an obturator distal end portion being released into a disposal container and with portions broken away to emphasize details;

FIGS. 8 and 9 are perspective views of a disposal container which sequentially illustrates the removal of a used or dull obturator distal end portion for the embodiment of trocar assembly shown in FIG. 7 wherein:

FIG. 8 is a perspective view of the disposal container with a portion of the obturator distal end portion (of the trocar assembly of FIG. 7) placed within the disposal container, and which omits details of the detent means to emphasize other details;

FIG. 9 is a perspective view of the disposal container closed about the obturator distal end portion and with the obturator's proximal portion separated from the obturator's distal end portion;

FIG. 11 is a top view of a portion of a third embodiment of trocar assembly according to the present invention illustrating the distal end portion of the obturator;

FIG. 12 is a top view of another portion of a third embodiment of trocar assembly according to the present invention illustrating the proximal end portion of the obturator and with portions broken away to show details;

FIG. 13 is a side view of the distal end portion shown in FIG. 11 taken approximately ninety (90) degrees from that view; and FIG. 14 is a side view of the proximal end portion of FIG. 12 taken approximately ninety (90) degrees from that view.

DETAILED DESCRIPTION OF THE PREFERRED EMBODIMENTS

Figure 1:
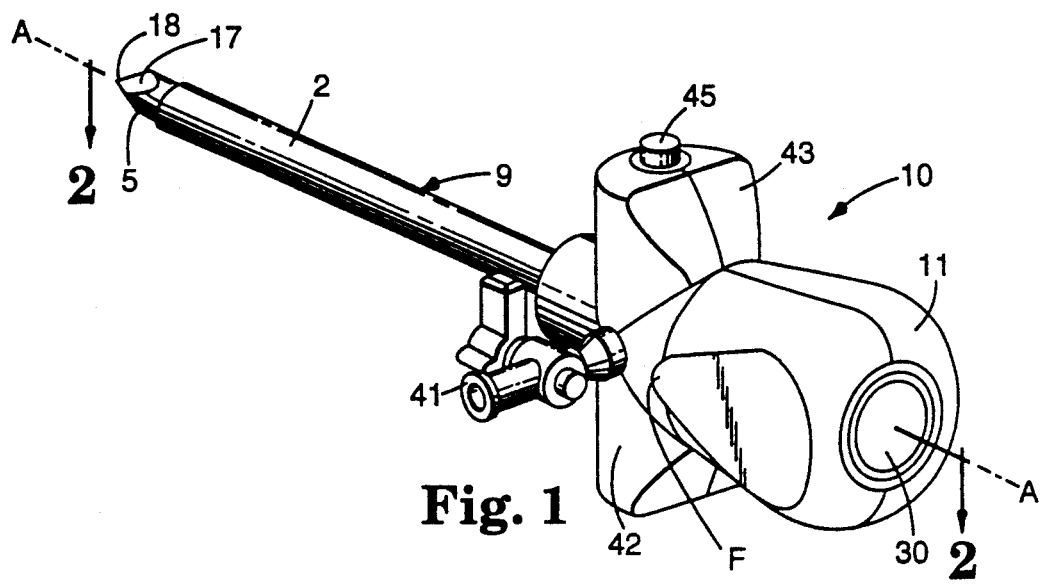
FIG. 1 is a perspective view of a first embodiment of trocar assembly according to the present invention that is placed within a cannula assembly that includes a valve which affords passage of insufflating gas into the body cavity and which restricts loss of insufflating gas from the body cavity when the trocar assembly is removed from the cannula assembly.

Referring now to FIGS. 1, 2 and 4 and 5 of the drawing there is shown an embodiment of a trocar device or assembly generally designated by reference character 10. The trocar assembly 10 is preferably used in laparoscopic surgery, however, the trocars described herein may also be used in other surgeries such as orthopedic surgery or in closed wound drainage applications.

FIG. 1 illustrates the trocar assembly 10 placed within a cannula assembly 9 which includes a cannula 2. The trocar assembly 10 may be completely removed from the cannula assembly 9 by sliding the trocar assembly 10 longitudinally relative to the cannula assembly 9.

The trocar assembly 10 is adapted for placement within the cannula 2 to facilitate inserting the cannula 2 through a wall 4 (FIG. 2) having tissue defining a body cavity 6. For example the trocar assembly 10 may be used to insert an access tube or cannula 2 through an abdominal wall of a patient.

The cannula 2 comprises interior surfaces 3 defining a lumen and a distal end 5 having an opening. The cannula 2 has an enlarged fixture formed from left and right portions 42 and 43. The fixture has a chamber at its proximal end. There is an opening at the proximal end of the chamber through which the trocar fits while the cannula 2 is inserted in the body cavity, and through which surgical instruments can access the interior of the body cavity after the cannula 2 is in place and the trocar assembly is removed.

Figure 3:
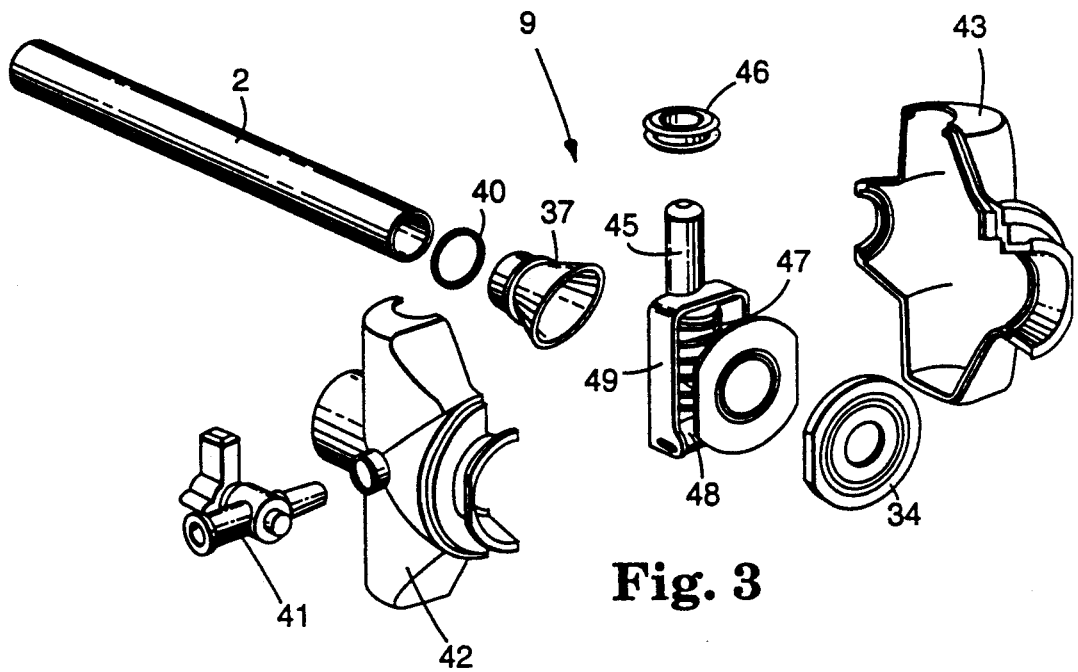
FIG. 3 is an exploded, enlarged perspective view of portions of the cannula assembly of FIG. 1.

FIG. 3 is an exploded perspective view of the cannula assembly 9. The cannula assembly 9 is the type which affords passage of insufflation gas through valve 41 to inflate the abdominal cavity and which restricts the passage of insufflation gas from the abdominal cavity after the trocar assembly 10 has been removed from the cannula assembly 9.

The cannula assembly 9 is similar to the cannula assembly described in U.S. patent application No. 07/657,105, now U.S. Pat. No. 5,152,754, the entire contents of which are herein expressly incorporated by reference. As best seen in FIG. 3, the cannula assembly 9 includes first 42 and second 43 housing or handle portions which may be assembled by a snap fit with a suitable adhesive (e.g. a "Prism" T. M. Loctite adhesive generally available from Loctite corporation of Newington, Conn.) to form a chamber 44. There is an opening at the proximal end of the chamber 44 through which the trocar fits while the access tube or cannula 2 is inserted in the body cavity, and through which surgical instruments can access the interior of the body cavity after the cannula 2 is in place and the trocar is removed.

A trap door valve member 48 having a sealing gasket is pivotally mounted adjacent the opening to close the opening. The valve member 48 is operated by a pushbutton 45 mounted for movement relative to first and second handle portions 42, 43. The pushbutton 45 is reciprocally mounted in a sealing gasket 46, and is resiliently spring biased outwardly by spring 47.

A link 49 extends from the pushbutton 45 to the valve member 48. Manually pushing the pushbutton 45 inwardly moves the valve member 48 open. The bias of the spring 47 causes the button 45 to move outwardly when it is release thereby causing the valve member 48 to close. The cannula assembly 9 also includes an insertion funnel guide adapter 37, an adapter seal stabilizer 34 and an O-ring 40.

The trocar assembly 10 comprises a handle 11 with a generally rounded configuration that can be comfortably gripped by the user. The handle 11 may be placed adjacent the chamber in the cannula assembly 9, and may comprise first and second polymeric portions which may be assembled by a snap fit with a suitable adhesive (e.g. a suitable "Prism" T.M. Loctite adhesive generally available from Loctite Corporation of Newington, Conn.).

The handle 11 is releasably, frictionally attached to the cannula assembly 9 so that after the trocar 10 inserts the cannula 2 in the wall 4, the trocar 10 can be removed so that the cannula 2 can be used to introduce surgical instruments into the body cavity. The handle 11 optionally includes flanges F which cooperate with grooves on the first and second portions 42 and 43 to restrict relative rotation between the handle 11 and the cannula assembly 9.

The trocar assembly 10 also includes an obturator 12 extending from the handle 11 and having an imaginary axis A (FIG. 1). The obturator 12 comprises a proximal portion 14, and a distal end portion 15 comprising a base part 16 and having three generally planar surfaces 17 intersecting to form three cutting edges and a point 18 at the distal end of the obturator 12 adapted to pierce the wall 4.

Figure 10:
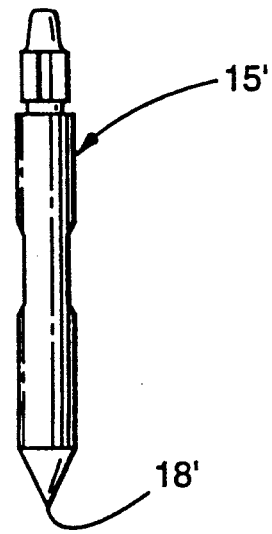
FIG. 10 is a side view of an obturator's distal end portion with a conical cutting portion.

FIG. 10 illustrates an alternative form of distal end portion 15' which includes a conical portion with a point 18'. Generally, the distal shape of the cutting surfaces of the obturator may take any suitable shape such as but not limited to triangular or square based pyramids or hollow parabolic, as long as the obturator is adapted to cut tissue.

The trocar assembly 10 also includes detent means 20 for releasably connecting the proximal portion 14 of the obturator to the distal end portion 15 of the obturator 12 and optionally for restricting relative rotation between the distal end portion 15 and the proximal portion 14. The detent means 20 comprises a groove part 22 extending at least partially about the axis A of the obturator 12 located on one of the proximal 14 and distal end 15 portions (in the species shown in FIGS. 1, 2, 4 and 5, the groove part 22 is located on the distal end portion 15) and a detent part 24 situated on the other of the proximal 14 and distal end 15 portions (in the species shown in FIGS. 1, 2, 4 and 5, the detent part 24 is located on the proximal part 14). The detent part 24 is adapted to releasably engage the groove part 22.

Figure 2:
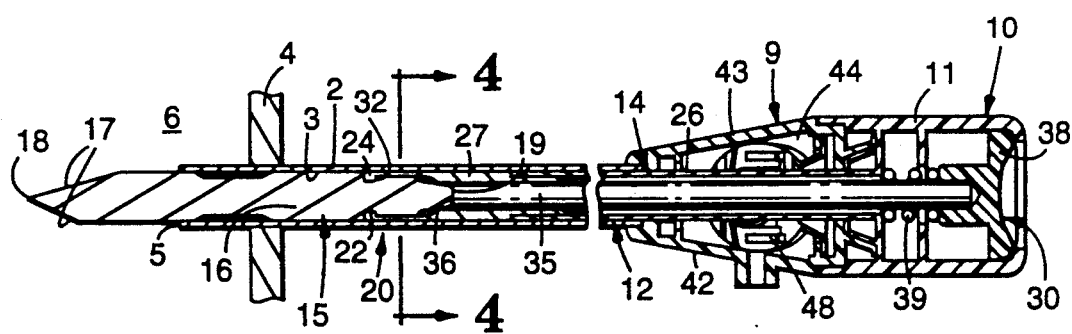
FIG. 2 is a slightly enlarged sectional view of the trocar and cannula assemblies shown in FIG. 1 with portions broken away or omitted to show details.

When the obturator 12 is placed within the cannula 2, the groove part 22 and the detent part 24 are situated within the lumen of the cannula 2 and the cutting edges project beyond the distal end 5 of the cannula 2 (see FIG. 2).

Figure 4:
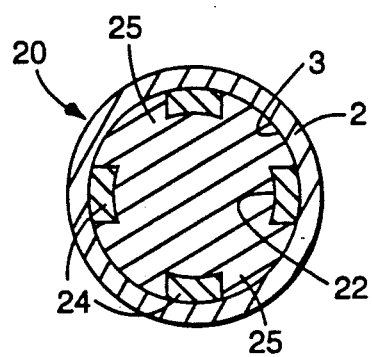
FIG. 4 is an enlarged sectional view of the first embodiment of trocar assembly and the cannula assembly shown in FIG. 2, taken approximately along lines 4—4 of FIG. 2.
Figure 5A:
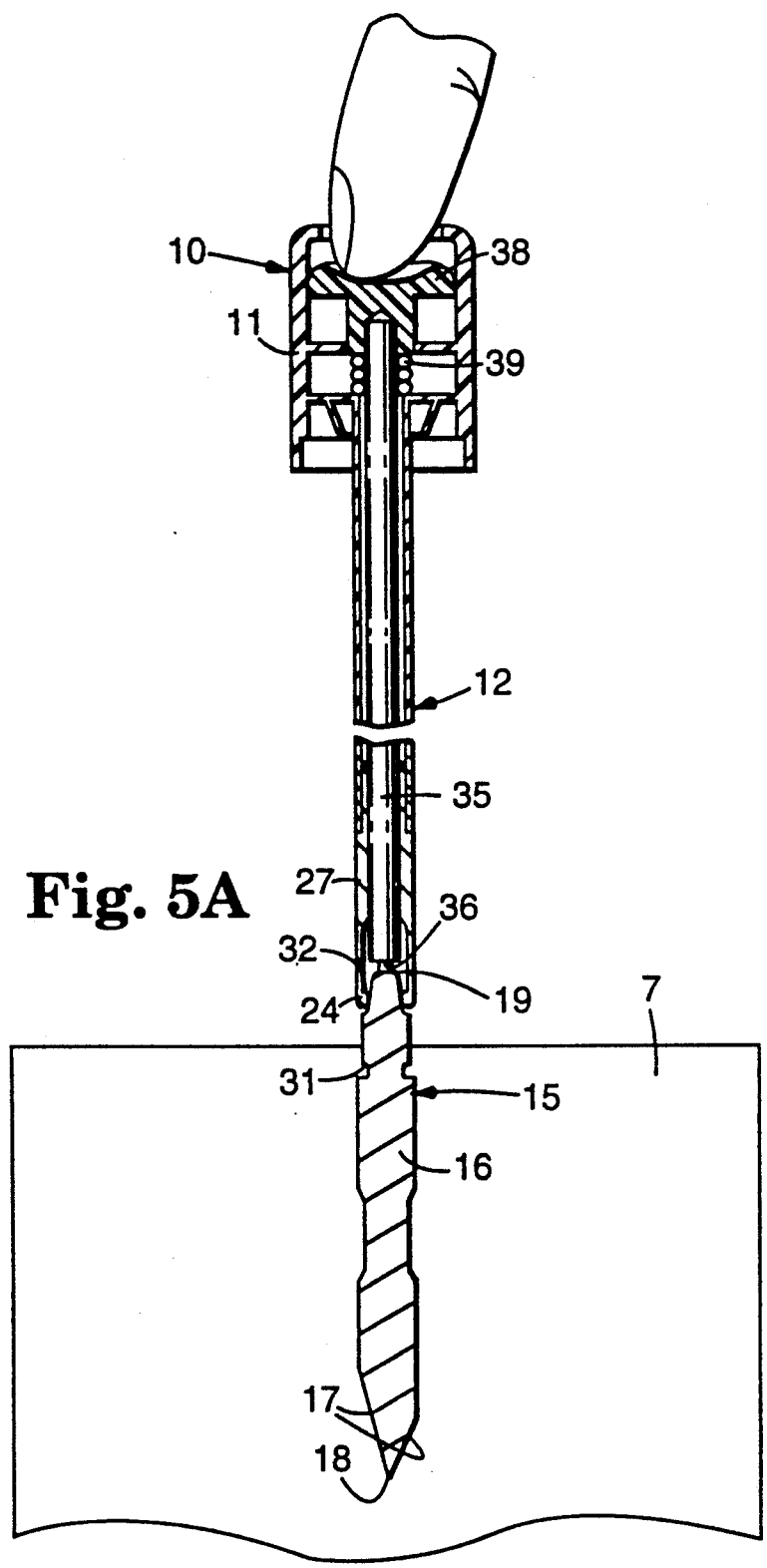
FIG. 5A is a sectional view of the trocar assembly of FIG. 1 removed from the cannula assembly and illustrating an obturator distal end portion that is released into a disposal container.

As best seen in FIG. 2, 4 and 5, the detent means 20 comprises a plurality of detent parts 24 having leaf spring members 27 movable radially outwardly (see FIG. 5) to accept or release the groove part 22 on the distal end portion 15. When the trocar assembly 10 is placed within the cannula 2, the interior or inside surfaces 3 defining the cannula lumen prevent the leaf spring members 27 from moving or deflecting radially outwardly to prevent release of the distal end portion 15 from the proximal portion 14. This prevents the distal end portion 15 from being accidently or inadvertently dropped into the body cavity 6 during a surgical procedure.

As shown in FIGS. 2, 4 and 5, the proximal portion 14 may comprise a housing member 26 constructed from any suitable material such as stainless steel, a polycarbonate or polypropylene. The proximal portion 14 also includes the leaf spring members 27 (which has the detent 24) which may be constructed from any suitable, flexible material such as, but not limited to a stainless steel, polycarbonate or polypropylene. The leaf spring members 27 may be adhesively attached to the housing member 26.

The leaf spring members 27 should be flexible enough to afford radially outward movement so that the distal end portion 15 may be received and yet resilient enough to allow the detent part 24 to spring back into engagement with the groove 22.

The distal end portion 15 may be constructed from any suitable material such as but not limited to a stainless steel, polycarbonate or polypropylene. Aluminum may also be used to construct the distal end portion 15. Since, the distal end portion is disposable, the material used to construct the distal end portion 15 is preferably inexpensive yet affords construction of sufficiently sharp and durable cutting surfaces.

As best seen in FIG. 4, the groove part 22 includes a plurality of axially extending ribs 25. When the proximal portion 14 is attached to the distal end portion 15 (as shown in FIGS. 1 and 4), the ribs 25 are situated between the leaf spring members 27 to restrict relative rotation between the proximal 14 and distal end 15 portions, and also between the distal end portion 15 and the cannula 2. Alternatively, the ribs 25 may be completely omitted from the embodiment shown in FIGS. 1, 2, 4 and 5.

Optionally, the trocar assembly 10 further includes means 30 for releasing the distal end portion 15 without requiring the user to grasp the distal end portion 15. The means 30 comprises the distal end portion 15 having camming surfaces 31, and the proximal portion 14 having bearing surfaces 32. The means 30 also includes an ejector rod 35 at least partially located within the proximal portion 14.

The ejector rod 35 is axially movable relative to the proximal portion 14. The ejector rod 35 has a distal end 36 adapted to abut a proximal end 19 of the distal end portion 15. The means 30 also includes a button member 38 mounted to the ejector rod 35. The button member 38 is axially movable between release (FIG. 5A) and rest/grasp (FIG. 2) positions. Between the rest/grasp and the release positions, the leaf spring members 27 deflect radially outwardly relative to the axis A taking the detent parts 24 out of engagement with the groove parts 22 to afford passage and release of the distal end portion 15 (see FIG. 5). A biasing means in the form of a coil spring 39 biases the button member 38 toward the rest position.

When the trocar assembly 10 is removed from the cannula 2, the button member 38 may be moved from the grasp to the release position so that the camming surfaces 31 may engage the bearing surfaces 32 and move portions of the leaf spring members 27 radially outwardly to release the distal end portion 15 (FIG. 5). It is important to again note that when the trocar assembly is located within the cannula assembly 9, the interior surfaces 3 of the cannula 2 prevent the leaf spring members 27 from deflecting radially outwardly.

Figure 6:
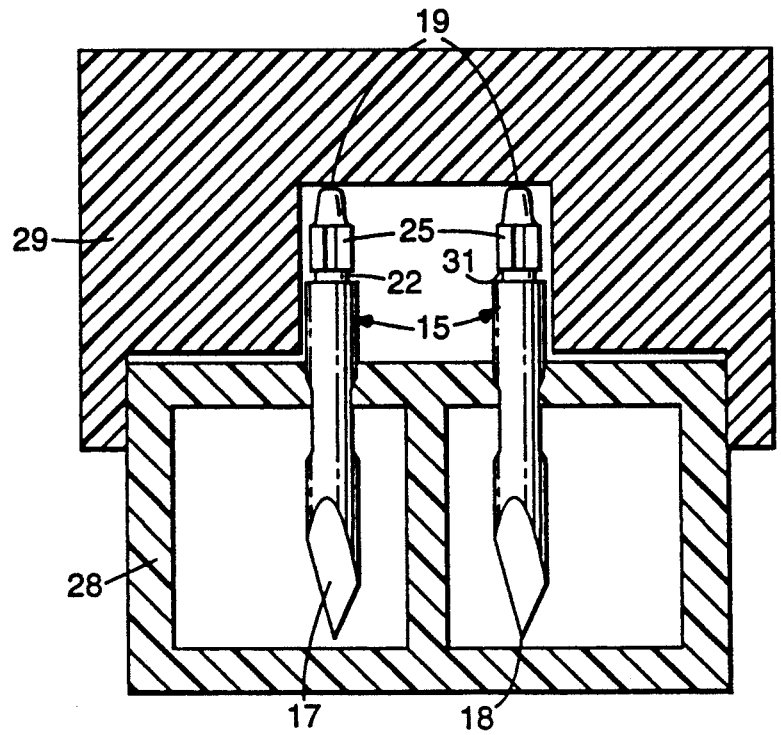
FIG. 6 is a side view which illustrates a rack of replacement distal end portions.

FIG. 6 illustrates a rack 28 of replacement distal end portions which may optionally include a cover 29. When the cover 29 is removed, the rack 28 exposes the proximal end 19 of a plurality of the replacement distal end portions 15 so that a user may conveniently slide the proximal end portion 14 onto the distal end portion 15 so that the detent part 24 engages the groove part 22. The rack 28 may include diverse distal end designs (e.g. distal tips with different shaped cutting surfaces such as conical, pyramidal etc.) according to the needs of a particular surgical procedure.

OPERATION

The trocar assembly 10 will be used to describe a method according to the present invention. The trocar assembly 10 optionally includes a protective cap (not shown) over the point 18 that is removed prior to use of the trocar assembly 10. The cannula 2 is initially installed over the distal end of the trocar assembly 10. The user grasps the handle 11 and first and second portions 42 and 43 of the trocar and cannula assemblies 9 and 10 with the palm of the hand.

The trocar assembly 10 is then advanced against the wall 4 of a patient (FIG. 2). The user continues to advance the trocar assembly 10 until the wall 4 is penetrated. As the wall 4 is being penetrated, the interior surfaces 3 of cannula 2 prevents the leaf spring parts 27 from springing radially outwardly to restrict the opportunity for the distal end portion 15 from inadvertently or accidently falling into the abdominal cavity 6.

Once the cannula 2 has penetrated through the wall 4, the user may then grasp the first and second portions 42 and 43 of the cannula assembly 9, and pull the trocar handle 11 axially and proximally relative to the cannula 2, leaving the cannula 2 in the abdominal wall 4. As noted above, the cannula assembly 9 may have a trapdoor valve that closes the cannula 2 when the trocar is withdrawn to prevent the escape of insufflation gas from the abdomen.

The trocar 10 can be quickly prepared for reuse (on the same patient) by pressing the button member 38 and allowing the used distal end portion 15 to fall into a disposal container 7 (FIGS. 5 and 5A), and then snapping another, replacement distal end portion 15 with sharp cutting surfaces onto the proximal portion 14. Optionally, the trocar assembly 10 may be sterilized, if necessary, by techniques well known in the art such as Gamma Radiation, steam or Ethylene Oxide (EtO) gas sterilization. Another cannula 2 can then be placed over the trocar assembly 10, and the procedure repeated on the same or a different patient. This procedure affords a clean, sharp distal tip end portion 15 which requires minimal handling by medical personnel.

Figure 7:
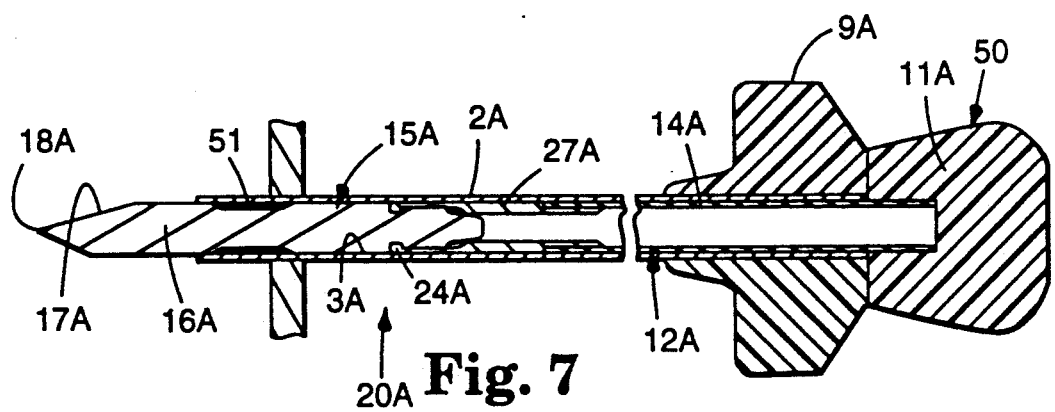
FIG. 7 is a sectional view of a second embodiment of trocar assembly according to the present invention and a cannula assembly.
Figure 8:
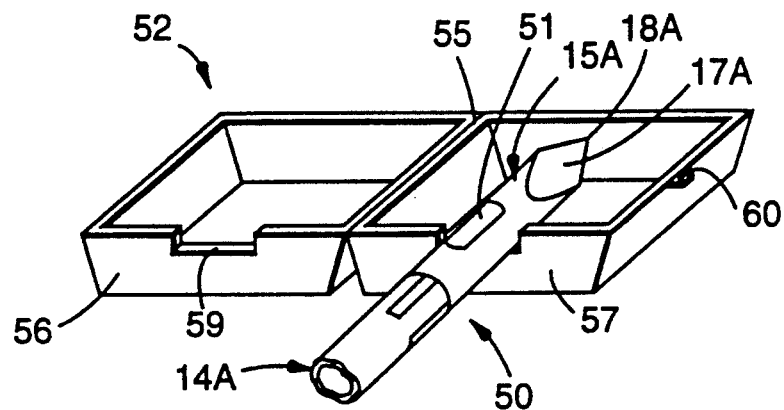
Figure 9:
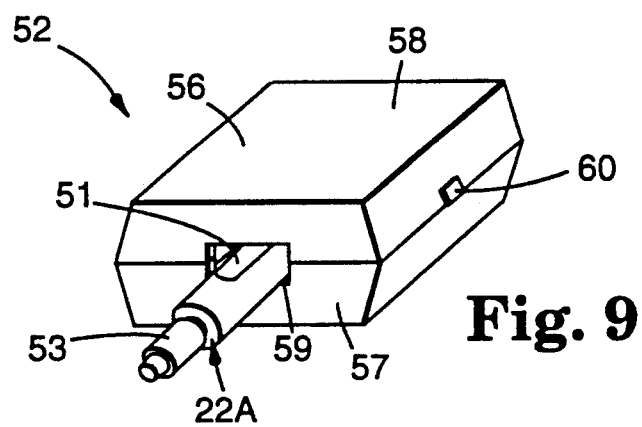

Referring now to FIGS. 7, 8 and 9 of the drawing, there is shown a second alternative embodiment of trocar assembly according to the present invention, generally designated by the reference character 50.

The assembly shown in FIG. 7 includes the trocar assembly 50 and a cannula assembly 9A (including cannula 2A). Unlike the cannula assembly 9, the cannula assembly 9A does not include a trap door for preventing the escape of insufflating gas.

The trocar assembly 50 has many elements which are essentially the same or identical as elements in the trocar assembly 10 which are identified by the same reference character to which the suffix "A" has been added.

The trocar assembly 50 comprises a handle 11A that is releasably, frictionally attached to the cannula assembly 9A. The trocar assembly 50 also includes an obturator 12A extending from the handle 11A. The obturator 12A comprises a proximal portion 14A, and a distal end portion 15A comprising a base part 16A and having three generally planar surfaces 17A intersecting to form three cutting edges and a point 18A. optionally, the trocar assembly 50 may include a cleanout or flush channel extending between the inner surfaces of the obturator 12A and a proximal end of the handle 11A.

The trocar assembly 50 also includes detent means 20A for releasably connecting the proximal portion 14A of the obturator to the distal end portion 15A of the obturator 12A. The detent means 20A comprises a groove part 22A located on one of the proximal 14A and distal end 15A portions and a detent part 24A situated on the other of the proximal 14A and distal end 15A portions.

The detent means 20A comprises a plurality of detent parts 24A having leaf spring members 27A movable radially outwardly to accept or release the groove part 22A on the distal end portion 15A. When the trocar assembly 50 is placed within the cannula 2A, the interior or inside surfaces 3A defining the cannula lumen prevent any portion of the leaf spring members 27A from moving or deflecting radially outwardly, and thus prevent release of the distal end portion 15A from the proximal portion 14A.

Unlike the trocar assembly 10, the trocar assembly 50 does not include the means 30. Instead the trocar assembly 50 uses engagable surfaces 51 located on the distal end portion 15A. For example, a user may manually engage the surfaces 51 and simply pull the proximal portion 14A axially relative to the distal end portion 15A to remove a used or dull distal end portion.

Also unlike the trocar assembly 10 and as best seen in FIG. 9, the distal portion 15A of the obturator 12A does not include ribs 25 and instead has a cylindrical portion 53. The detents 24 and the leaf spring members 27A are not obstructed and thus, the distal portion 15A is free to rotate relative to the cannula 2A and proximal portion 14A to afford a "drilling action" preferred by some surgeons.

The engagable surfaces 51 are spaced from the cutting edges and are adapted to be grasped by a user. When the trocar assembly 50 is removed from the cannula, a user may manually grasp the distal end portion 15A by the engagable surfaces 51 and pull the distal end portion 15A away from the proximal portion 14A to cause the leaf spring members 27A to move radially outwardly to release the distal end portion 15.

FIGS. 8 through 9 illustrate an alternative, preferred method of removing the distal end portion 15A from the proximal portion 14A of the trocar assembly 50 which includes a means for releasing the distal end portion without requiring the user to grasp the distal end portion generally designated by reference character 52.

The means 52 comprises a disposal container having first 56 and second 57 sections each having manually engagable outer surfaces 58 and distal end portion engaging surfaces 59 spaced from the manually engagable outer surfaces 58. The disposal container includes hinge 55 and latch 60. The disposal container is preferably integrally constructed from an inexpensive material such as, but not limited to a polycarbonate, so long as it acts as a barrier to prevent the cutting surfaces of the obturator from coming into contact with a person (e.g. such as a surgeon or processor of medical waste).

The disposal container's first 56 and second 57 portions are movable between an open position (FIG. 8) where they receive a distal end portion 15A of trocar assembly 50 and a closed position (FIG. 9). In the closed position, (1) the distal end portion engaging surfaces 59 grasp portions of the distal end portion (e.g. the engagable surfaces 51), (2) the disposal container encloses the cutting surfaces of the distal end portion 15A and provides a barrier to restrict exposure to the cutting surfaces, and (3) a user may grasp the manually engagable surfaces 58 of the disposal container and move the disposal container axially away from the proximal portion 14A of the trocar assembly 50 to separate the distal end portion 15A from the proximal portion 14A without requiring the user to grasp the distal end portion 15A.

Referring now to FIGS. 11 through 14 of the drawing, there is shown a third alternative embodiment of trocar assembly according to the present invention, generally designated by the reference character 100.

The trocar assembly 100 is adapted for use with cannula assemblies similar to the cannula assemblies 9 and 9A. The trocar assembly 100 comprises a handle (omitted to show detail but similar to 11 or 11A) that is releasably, frictionally attached to the cannula assembly. The trocar assembly 100 also includes an obturator 112 extending from the handle. The obturator 112 comprises a proximal portion 114, and a distal end portion 115 comprising a base part 116 and having three generally planar surfaces 117 intersecting to form three cutting edges and a point 118. Alternatively the cutting surfaces may comprise any suitable, desired shape.

The trocar assembly 100 also includes detent means 120 for releasably connecting the proximal portion 114 of the obturator to the distal end portion 115 of the obturator 112. The detent means 120 comprises a groove part 122 located on one of the proximal 114 and distal end 115 portions (in FIGS. 12 and 14, the groove part 112 is shown on the proximal portion 114) and a detent part 124 situated on the other of the proximal 114 and distal end 115 portions (in FIGS. 11 and 13, the detent part 124 is shown on the distal portion 115).

The detent part 124 comprises two lug portions 126 and 127. The lug portion 126 has a semicylindrical outer surface sharing an axis with the axis A' of the obturator 112. The lug portion 127 may also have a semicylindrical outer surface that does not share an axis with the obturator 112, or alternatively, as shown in FIG. 13, the lug portion 127 may simply be a flat surface.

To construct the obturator 112, the distal end portion 115 would be placed into the proximal portion 114 from the side or top and then the obturator 112 would be placed within the lumen of a cannula assembly where the interior surfaces of the cannula assembly (e.g. 3 or 3A) would "lock" the distal end portion in place. The lug 126 is believed to restrict or prevent rotation of the distal end portion 115 from rotating relative to the proximal portion or the cannula assembly.

The present invention has now been described with reference to several embodiments thereof. It will be apparent to those skilled in the art that many changes or additions can be made in the embodiments described without departing from the scope of the present invention. For example, the trocar assembly 50 may include ribs similar to the ribs 25 shown in FIG. 4; and the cannula assembly 9A shown in FIG. 7 may be replaced with a cannula assembly which is substantially identical to the cannula assembly 9 shown in conjunction with the first embodiment of trocar assembly 10 (e.g. it may include a trap door valve mechanism, etc.). Additionally the trocar assembly 10 may be used in conjunction with a cannula assembly similar to the cannula assembly 9A. Also, the detent part 24 of the trocar assembly 10 may be located on the distal end portion 15 and the groove part 22 may be located on the proximal portion 14. Thus, the scope of the present invention should not be limited to the structures described in this application, but only by structures described by the language of the claims and the equivalents of those structures.

What is claimed is:

1. A trocar assembly for placement in a cannula to facilitate inserting the cannula through a wall having tissue defining a body cavity, which cannula comprises interior surfaces defining a lumen and a distal end having an opening, the trocar assembly comprising:
   a handle;
   an obturator extending from said handle and having an imaginary axis,
   said obturator comprising:
      a proximal portion, and
      a distal end portion comprising a base part and having three generally planar surfaces intersecting to form three cutting edges and a point at the distal end of the obturator adapted to pierce the wall defining the body cavity, and
   detent means for releasably connecting said proximal portion of said obturator to said distal end portion of said obturator and for restricting relative rotation between said distal end portion and said proximal portion comprising:
      a groove part extending about the axis of the obturator located on one of the proximal and distal end portions and
      a detent part situated on the other of the proximal and distal end portions and adapted to engage the groove part,
   wherein when the obturator is placed within the cannula, the groove part and the detent part are situated within the lumen of the cannula and the cutting edges project beyond the distal end of the cannula.

2. A trocar assembly according to claim 1 wherein the proximal portion has said detent part and the distal end portion has the groove part, and
   said detent means comprises a plurality of detent parts having leaf spring members movable radially outwardly to accept or release the groove part on the distal end portion, and the groove part includes a plurality of axially extending ribs adapted to be situated between the leaf spring members to restrict relative rotation between the proximal and distal end portions;
   wherein when the trocar assembly is placed within the cannula, the interior surfaces defining the cannula lumen prevent the leaf spring members from moving radially outwardly to prevent release of the distal end portion, and
   when the trocar assembly is removed from the cannula, the obturator's distal end portion may be removed from the proximal portion by moving the distal end portion axially relative to the proximal portion.

3. A trocar assembly according to claim 2 wherein the trocar assembly further includes means for releasing the distal end portion without requiring the user to grasp the distal end portion comprising:
   the distal end portion having camming surfaces, the proximal portion having bearing surfaces, an ejector rod at least partially located within the proximal portion and axially movable relative to the proximal portion, said ejector rod having a distal end adapted to abut a proximal end of the distal end portion, and
   a button member mounted to the ejector rod and movable between a release and a rest position,
   biasing means for biasing the button member toward said rest position,
   wherein when said trocar assembly is removed from said cannula, said button member may be moved from said rest to said release position so that said camming surfaces may engage said bearing surfaces and move said leaf spring members radially outwardly to release said distal end portion.

4. A trocar assembly according to claim 1 wherein said distal end portion comprises manually engagable surfaces spaced from said cutting edges and adapted to be grasped by a user,
   the proximal portion has said detent part and the distal end portion has the groove part,
   said detent means comprises a plurality of detent parts having leaf spring members movable radially outwardly to accept or release the groove part on distal end portion, and the groove part includes a plurality of axially extending ribs adapted to be situated between the leaf spring members to restrict relative rotation between the proximal and distal end portions,
   wherein when the trocar assembly is placed within the cannula, the interior surfaces defining the cannula lumen prevent the leaf spring members from moving radially outwardly to prevent release of the distal end portion, and
   wherein when the trocar assembly is removed from said cannula, a user may manually grasp the distal end portion by the manually engagable surfaces and pull the distal end portion away from the proximal portion to cause the leaf spring engagement members to move radially outwardly to release the distal end portion.

5. A trocar assembly according to claim 1 wherein the detent means comprises a lug, and
   when the obturator is placed within the cannula, interior surfaces of the cannula lock the lug within the groove.

6. A trocar assembly for placement in a cannula to facilitate inserting the cannula through a wall having tissue defining a body cavity, which cannula comprises interior surfaces defining a lumen and a distal end having an opening, the trocar assembly comprising:
   a handle;
   an obturator extending from said handle and having an imaginary axis,
   said obturator comprising:
      a proximal portion, and
      a distal end portion comprising a base part and having cutting surfaces adapted to pierce the wall defining the body cavity, and
   detent means for releasably connecting said proximal portion of said obturator to said distal end portion of said obturator comprising:
      a groove part extending at least partially about the axis of the obturator located on one of the proximal and distal end portions and a detent part situated on the other of the proximal and distal end portions and adapted to engage the groove part,
   wherein when the obturator is placed within the cannula, at least a portion of the groove part and the detent part are situated within the lumen of the cannula and the cutting surfaces project beyond the distal end of the cannula, and
   when the obturator is removed from the cannula, the distal end portion is adapted to be quickly and conveniently removed from the proximal portion.

7. A trocar assembly according to claim 6 wherein the proximal portion has said detent part and the distal end portion has the groove part, and said detent means comprises a plurality of detent parts having leaf spring members movable radially outwardly to accept or release the groove part on the distal end portion, and wherein when the trocar assembly is placed within the cannula, the interior surfaces defining the cannula lumen prevent the leaf spring members from moving radially outwardly to prevent release of the distal end portion.

8. A trocar assembly according to claim 6 wherein the trocar assembly further includes means for releasing the distal end portion without requiring the user to grasp the distal end portion.

9. A trocar assembly according to claim 8 wherein said means for releasing the distal end portion without requiring the user to grasp the distal end portion the distal end portion having camming surfaces, the proximal portion having bearing surfaces, an ejector rod at least partially located within the proximal portion and axially movable relative to the proximal portion, said ejector rod having a distal end adapted to abut a proximal end of the distal end portion, and a button member mounted to the ejector rod and movable between a release and a rest position, biasing means for biasing the button member toward said rest position, wherein when said trocar assembly is removed from said cannula, said button member may be moved from said rest to said release position so that said camming surfaces may engage said bearing surfaces and move said leaf spring members radially outwardly to release said distal end portion.

10. A trocar assembly according to claim 7 wherein said means for releasing the distal end portion without requiring the user to grasp the distal end portion comprises:

a disposal container having first and second sections each having manually engagable outer surfaces and distal end portion engaging surfaces spaced from said manually engagable outer surfaces;

wherein the disposal container's first and second portions are movable between an open position adapted to receive a distal end portion of a trocar assembly and a closed position in which (1) the distal end portion engaging surfaces grasp portions of the distal end portion, (2) the disposal container encloses the cutting surfaces of the distal end portion and provides a barrier to restrict the user's exposure to the cutting surfaces, and (3) a user may grasp the manually engagable surfaces of the disposal container and move the disposal container axially away from the proximal portion of the trocar assembly to separate the distal end portion from the proximal portion.

11. A trocar assembly according to claim 7 wherein said distal end portion comprises manually engagable surfaces spaced from said cutting edges and adapted to be grasped by a user, the proximal portion has said detent part and the distal end portion has the groove part, said detent means comprises a plurality of detent parts having leaf spring members movable radially outwardly to accept or release the groove part on the distal end portion, and the groove part includes a plurality of axially extending ribs adapted to be situated between the leaf spring members to restrict relative rotation between the proximal and distal end portions,, wherein when the trocar assembly is placed within the cannula, the interior surfaces defining the cannula lumen prevent the leaf spring members from moving radially outwardly to prevent release of the distal end portion, and wherein when the trocar assembly is removed from said cannula, a user may manually grasp the distal end portion by the manually engagable surfaces and pull the distal end portion away from the proximal portion to cause the leaf spring members to move radially outwardly to release the distal end portion.

12. A trocar assembly according to claim 6 wherein the groove part includes a plurality of axially extending ribs adapted to be situated between the leaf spring members to restrict relative rotation between the proximal and distal end portions.

13. A trocar assembly according to claim 6 wherein the detent means comprises a lug, and when the obturator is placed within the cannula, interior surfaces of the cannula lock the lug within the groove.

14. A method of using a trocar assembly comprising the steps of:

providing a cannula comprising interior surfaces defining a lumen and a distal end having an opening, providing the trocar assembly comprising a handle, an obturator extending from said handle and having an imaginary axis, the obturator comprising a proximal portion, and a distal end portion comprising cutting surfaces, and detent means for releasably connecting said proximal portion of said obturator to said distal end portion of said obturator comprising a groove part extending about the axis of the obturator located on one of the proximal and distal end portions and a detent part situated on the other of the proximal and distal end portions and adapted to engage the groove part, placing the obturator within the cannula such that at least a portion of the groove part and the detent part are situated within the lumen of the cannula and the cutting surfaces project beyond the distal end of the cannula, and such that the interior surfaces of the cannula prevent the detent means from releasing the connection between the proximal portion and the distal portion, inserting the cannula through a wall having tissue defining a body cavity, then removing the used or dull distal end portion, and replacing the used or dull distal end portion of the obturator with a different distal end portion.

15. A method of using a trocar assembly according to claim 14 wherein the step of removing the used or dull distal end portion comprises the step of:

releasing the distal end portion without requiring the user to grasp the distal end portion.

16. A method of using a trocar assembly according to claim 15 wherein the step of releasing the distal end portion without requiring the user to grasp the distal end portion comprises:

providing the distal end portion with camming surfaces, providing the proximal portion with bearing surfaces, providing an ejector rod at least partially located within the proximal portion and axially movable relative to the proximal portion, providing the ejector rod with a distal end adapted to abut a proximal end of the distal end portion, and providing a button member mounted to the ejector rod and movable between a release and a rest position, biasing the button member toward the rest position, removing the trocar assembly from the cannula, moving the button member from the rest to the release position so that the camming surfaces engage the bearing surfaces and move the leaf spring members radially outwardly to release the distal end portion.

17. A method of using a trocar assembly according to claim 14 further including the step of preventing relative rotation between the distal end portion and the proximal portion of the obturator.

18. A method of using a trocar assembly according to claim 15 wherein the step of releasing the distal end portion without requiring the user to grasp the distal end portion comprises:

providing a disposal container having first and second sections each having manually engagable outer surfaces and distal end portion engaging surfaces spaced from said manually engagable outer surfaces;

placing the disposal container's a first and second portions in an open position, placing a part of the distal end portion of a trocar assembly against the distal end portion engaging surfaces, moving the disposal container's first and second portions to a closed position such that (1) the distal end portion engaging surfaces grasp portions of the distal end portion, and (2) the disposal container encloses the cutting surfaces of the distal end portion and provides a barrier to restrict the user's exposure to the cutting surfaces, grasping the manually engagable surfaces of the disposal container, and then moving the disposal container axially away from the proximal portion of the trocar assembly to separate the distal end portion from the proximal portion.

* * * * *